US011663428B2

(12) United States Patent
Sayles

(10) Patent No.: US 11,663,428 B2
(45) Date of Patent: May 30, 2023

(54) MULTI-STAGE CODE SCANNING FOR DATA TRANSFER

(71) Applicant: Summate Technologies, Inc., Newburyport, MA (US)

(72) Inventor: Philip William Sayles, Newburyport, MA (US)

(73) Assignee: Summate Technologies, Inc., Newburyport, MA (US)

(*) Notice: Subject to any disclaimer, the term of this patent is extended or adjusted under 35 U.S.C. 154(b) by 14 days.

(21) Appl. No.: 17/324,736

(22) Filed: May 19, 2021

(65) Prior Publication Data

US 2022/0374622 A1 Nov. 24, 2022

(51) Int. Cl.
G06K 7/14 (2006.01)
G16H 40/40 (2018.01)

(52) U.S. Cl.
CPC ........... *G06K 7/1408* (2013.01); *G16H 40/40* (2018.01)

(58) Field of Classification Search
CPC ...... G06K 7/1408; G16H 40/40; G16H 20/40; G16H 40/20; G06Q 50/22
See application file for complete search history.

(56) References Cited

U.S. PATENT DOCUMENTS

2005/0038556 A1* 2/2005 Gagnon ................. G16H 40/20
700/226
2008/0030345 A1* 2/2008 Austin .................. A61B 90/98
340/539.1
2009/0317002 A1* 12/2009 Dein ...................... A61B 90/90
340/568.1
2014/0263674 A1* 9/2014 Cerveny .......... G06K 19/06037
235/494
2014/0303606 A1* 10/2014 Garner-Richards ........................
A61B 17/06114
606/1

(Continued)

FOREIGN PATENT DOCUMENTS

CN 103903025 A * 7/2014
CN 205845048 U * 12/2016
CN 107918871 A * 4/2018

OTHER PUBLICATIONS

CN103903025A, Method and system for transmitting source tracing information during domestic animal slaughtering and splitting, 5 pages. (Year: 2022).*

(Continued)

Primary Examiner — Tuyen K Vo
(74) Attorney, Agent, or Firm — Blueshift IP, LLC; Robert Plotkin

(57) ABSTRACT

A first signal is ready from a first machine-readable object, which may be part of a peg stored in a surgical asset tray. A first part number of a first surgical asset is identified based on the first signal. A label is printed to include a first machine-readable visual indicia representing the first part number. A second signal is optically read from the first machine-readable visual indicia. The first part number of the first surgical asset is identified based on the second signal. The first part number of the first surgical asset is stored in a non-transitory computer-readable medium. This method enables information about surgical assets used in the field to be transferred from machine-readable objects into electronic data stores efficiently, effectively, and semi-automatically.

20 Claims, 4 Drawing Sheets

(56) References Cited

U.S. PATENT DOCUMENTS

2022/0160439 A1\* 5/2022 Ryan ..................... A61B 90/98

OTHER PUBLICATIONS

CN107918871A, Application method of two-dimensional barcode implanted medical instrument tracking, 3 pages. (Year: 2022).\*
CN205845048U, Surgical instrument information tracing device, 3 pages. (Year: 2022).\*

\* cited by examiner ing to embodiments of the present invention will become apparent from the following description and from the claims.
MULTI-STAGE CODE SCANNING FOR DATA TRANSFER

BACKGROUND

Modern surgical procedures involve the use of a wide variety of supplies and implants, such as screws, plates, Kirschner wires (K-wires), anchors, and drill bits. It is critical to track and create a record of the type and quantity of the supplies used both inside and outside of the field during a particular surgical procedure for a variety of reasons, such as billing, quality assurance, accurate patient records, and determining the type and quantity of supplies that need to be reordered and restocked. Creating such an accurate record while a surgery is being performed is complicated by a variety of factors, including the wide variety of supplies that are used, difficulty of tracking what is used inside the sterile field, the lack of space on the tray to print the corresponding part number of each distinct screw type, the small size of such supplies, and the difficulty of distinguishing similar supplies from each other, all in real-time while the surgery is being performed.

Traditional manual methods for tracking such supply usage, such as visually identifying the supplies that are used and writing down the type and quantity of such supplies on paper or manually recording such supplies in a database, tend to be slow, tedious, and error-prone. Furthermore, optical scanning technology, such as direct part marking using barcodes on the supplies, has proven to be challenging to implement, due to the nature of the implants. For example, implants often are made of polished stainless steel, are highly reflective, can be very small, have only irregular surfaces (such as the head of a screw), and are subject to a very harsh reprocessing environment (e.g., heat, steam, and chemicals). All of these factors have made it challenging to directly mark implants. It can also be difficult to read such markings under the bright lights of the surgical field during surgery.

Errors in the record of the type and quantity of supplies and implants used can have a variety of negative consequences, including failure of the hospital to be reimbursed for all of the supplies that were used, failure to reorder the correct supplies as a result of inflated inventory levels resulting from failure to accurately record supplies used in the field, lag time in ordering restock supplies in a timely fashion, and errors in the patient's surgical history which can contribute to suboptimal care for the patient in the future.

What is needed, therefore, are improved techniques for tracking the type and quantity of supplies used during surgery.

SUMMARY

A first signal is read from a first machine-readable object, which may be part of a peg stored in a surgical asset tray. A first part number of a first surgical asset is identified based on the first signal. A label is printed to include a first machine-readable visual indicia representing the first part number. A second signal is optically read from the first machine-readable visual indicia. The first part number of the first surgical asset is identified based on the second signal. The first part number of the first surgical asset is stored in a non-transitory computer-readable medium. This method enables information about surgical assets used in the field to be transferred from machine-readable objects into electronic data stores efficiently, effectively, and semi-automatically.

Other features and advantages of various aspects and embodiments of the present invention will become apparent from the following description and from the claims.

DETAILED DESCRIPTION

As described above, the state of the art for recording the use of assets in the surgical field is to perform such recording manually. The surgical technician manually reads the microprinted part numbers on the assets, or on the tray itself next to the corresponding asset. In the case of some assets, such as tightly-packed screws, there is not enough room to print the part numbers on the tray or the caddy. The part numbers and other characteristics of the assets are usually written down on a sterile piece of paper, or on the surgical drape itself. Such manually-written characteristics are then manually matched against a pre-printed inventory sheet outside the sterile field to ascertain the correct part number. This manual process is then followed by a succession of subsequent manual processes, which include manual transcription and data entry steps to complete the recording of each removed asset. The entire process is tedious, time-consuming, and error prone.

Embodiments of the present invention provide an improvement to the process of recording asset usage. In particular, embodiments of the present invention are directed to systems and methods for enabling the use of an asset to be scanned at the time of use, in the field, during surgery, and for the information scanned from the asset to be entered into an electronic data store with minimal effort. Embodiments of the present invention overcome a problem which has hindered the development of such an improvement, namely that information about surgical assets is stored in various different systems (e.g., multiple databases) which do not communicate with each other directly, and that the information used to identify an asset in one such system often is different from the information that is used to identify the asset in another such system (e.g., one database may identify a particular asset using one identifier, while a second database may identify the same asset using a different identifier). As will be described in more detail below, embodiments of the present invention address these problems using a combination of reading information from tags associated with surgical assets (whether or not those tags are coupled to the surgical assets), printing information derived from the information that was read from the surgical assets, optically reading the printed information, and automatically entering data about the surgical assets based on the information that was optically read. These techniques significantly reduce the amount of human effort required to enter information about surgical assets into an electronic data store, and also reduce or eliminate data entry error by reducing or eliminating the need for human data entry in the process.

Figure 1A:
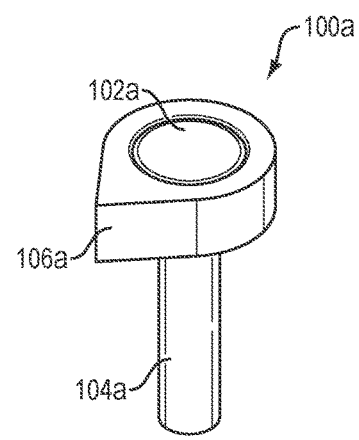
FIGS. 1A and 1B are illustrations of labeled pegs according to embodiments of the present invention.

Referring to FIG. 1A, a labeled peg 100a according to one embodiment of the present invention is shown. The labeled peg 100a is described in more detail in U.S. Pat. No. 10,909,343, issued on Feb. 2, 2021, entitled, "Automated Screw Identification System and Method with Labeled Pegs," which is hereby incorporated by reference herein.

As will be described in more detail below, the peg 100a may be used to label assets in a surgical tray and to enable a method for recording the use of such assets in the surgical field in real-time. The peg 100a includes a cap piece 102a. The cap piece 102a is or contains a machine-readable object, which may take any of a variety of forms. For example, the machine-readable object may be or include any one or more of the following: a chip, a microprocessor, a non-transitory computer-readable memory, a barcode, or a data matrix code. Regardless of the form that the machine-readable object takes, the machine-readable object may contain data representing information about one or more surgical assets (e.g., screws). The data may, for example, represent any one or more of the following properties of one or more assets: manufacturer, model number, part number, stock keeping unit (SKU), length, and/or width. Those having ordinary skill in the art will understand how to encode such properties in a particular kind of machine-readable object, such as microprocessor, non-transitory computer-readable memory, barcode, or data matrix code.

The cap piece 102a may be implemented to have any of a variety of shapes and sizes. For example, in the particular embodiment illustrated in FIG. 1A, the cap piece 102a is in the shape of a disc. The cap piece 102a may, however, be in the shape of a wafer (e.g., with a square or rectangular top surface). These are merely examples and do not constitute limitations of the present invention. The cap piece 102a may be sufficiently transparent for laser energy to penetrate it to power a chip or other machine-readable object.

The cap piece 102a may, for example, enclose the machine-readable object. For example, the cap piece 102a may include a bottom layer (e.g., disc) and a top layer (e.g., disc), which may sandwich the machine-readable object in between so that the cap piece 102a includes the top layer followed by the machine-readable object followed by the bottom layer. The top and/or bottom layer may include a recess into which the machine-readable object may be placed. The recess(es) may have the same shape and a slightly larger size than the machine-readable object, so that the machine-readable object fits snugly within the recess(es).

The top and bottom layers may be secured to each other and thereby enclose the machine-readable object in any of a variety of ways, such as by using a mechanical joining process (e.g., heat staking or ultrasonic welding), thereby securing and protecting the enclosed machine-readable object against the harsh reprocessing environment. The top and/or bottom layers may be made of any material(s), such as a polymer (e.g., polycarbonate).

The peg 100a also includes a columnar protrusion 104a. The columnar protrusion 104a may, for example, be coupled to the bottom of the cap piece 102a. The columnar protrusion 104a extends downward from the cap piece 102a (whether or not coupled to the cap piece). The columnar protrusion 104a may, for example, extend in a direction that is perpendicular to the top and/or bottom surface of the cap piece 102a. Although the columnar protrusion 104a is shown in FIG. 1A as being in the shape of a column (i.e., having a circular cross-section for its entire length), this is merely an example and not a limitation of the present invention. Alternatively, for example, some or all of the length of the columnar protrusion may have a cross-section having a square, rectangular, diamond, or elliptical shape.

As shown in FIG. 1A, the peg 100a may also include a directional member 106a. The directional member 106a has a directional feature, which has a shape that points in a particular direction. In the particular embodiment illustrated in FIG. 1A, the directional feature is a side of the directional member 106a which tapers to a point. This, however, is merely an example of the directional feature and not a limitation of the present invention. Alternatively, for example, the directional feature may take the form of, or have a cross section in the shape of, an arrow, a square or cube, a rectangle or rectangular parallelepiped, a cone, or a circle, sphere, or column. Furthermore, pegs implemented according to embodiments of the present invention need not have any directional member.

The disc 102a may, for example, be coupled to the directional member 106a. Such a coupling may be implemented in any of a variety of ways, such as adhesive, heat staking, or ultrasonic welding. As one example, the directional member 106a may include a recess into which the disc 102a may be placed. The recess may have the same shape and a slightly larger size than the disc 102a, so that the disc 102a fits snugly within the recess.

In such embodiments, the directional member 106a may have a solid bottom surface to which the top of the columnar protrusion 104a is coupled. In other embodiments, the top of the columnar protrusion 104a may be coupled to the bottom of the disc 102a, and the columnar protrusion 104a (with the disc 102a coupled to its top end) may extend through a gap in the directional member 106a. The top surface of the disc 102a may be aligned with the top surface of the directional member 106a. In such embodiments, the columnar protrusion 104a may be fixed in place inside the gap in the directional member 106a in any of a variety of ways.

In yet other embodiments, the directional member 106a may be integrally formed with the columnar protrusion 104a, such as from a single material.

Figure 1B:
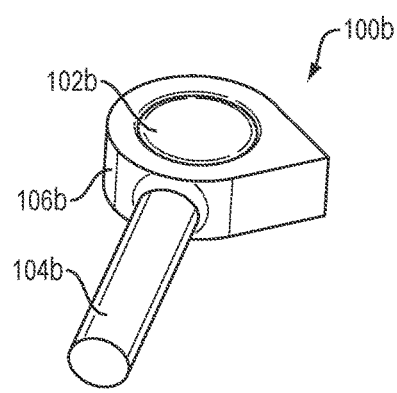

In the embodiment shown in FIG. 1A, the directional member 106a points in a direction that is perpendicular to the length of the columnar protrusion 104a, and the width (i.e., plane) of the disc 102a is perpendicular to the length of the columnar protrusion 104a. This is merely one example and does not constitute a limitation of the present invention. An alternative embodiment of a peg 100b is shown in FIG. 1B, which includes a disc 102b that may be implemented in the same manner as the disc 102a, and which includes a columnar protrusion 104b that may be implemented in the same manner as the columnar protrusion 104b. In the peg 100b of FIG. 1B, however, the directional member 106b still points in a direction that is perpendicular to the length of the columnar protrusion 104b, but the width (i.e., plane) of the disc 102a is parallel to the length directional member 106b. The different embodiments 100a and 100b shown in FIGS. 1A and 1B, respectively, may be useful in different applications, depending, for example, on the wide variety of footer layouts that exist in the many orthopedic trays currently in use.

Either of the columnar protrusions 104a-b may be designed to push into a hole that has been predrilled into a footer (which is typically, but not necessarily, made of silicon rubber) in the surgical tray. As another example, either of the columnar protrusions 104a-b may be designed to push into a corresponding hole in the rubber footer so that the disc 102a or 102b would sit flush with the corresponding surface of the footer.

Pegs other than those illustrated in FIGS. 1A and 1B fall within the scope of the present invention. For example, any of the pegs and/or asset trays disclosed in the following patents (all of which are incorporated by reference herein) may be used, in any combination, within embodiments of the present invention:

U.S. Pat. No. 10,470,809, issued on Nov. 12, 2019, entitled, "Automated Screw Identification System and Method"; and U.S. Pat. No. 10,786,331, issued on Sep. 29, 2020, entitled, "Automated Implant Identification System and Method with Combined Machine-Readable and Human-Readable Markers."

As disclosed therein, for example, a surgical asset tray may include a plurality of rows. The tray may include a plurality of slots at the tops of corresponding rows. Each of the plurality of rows may include a plurality of corresponding slots, which are adapted to receive and hold surgical assets. Within each of the rows, one of the slots holds a particular peg including a machine-readable object, such as a machine-readable peg, which contains data representing information about one or more of the surgical assets in that row, such as the type, length, and/or part number of surgical assets contained in that row.

Figure 2:
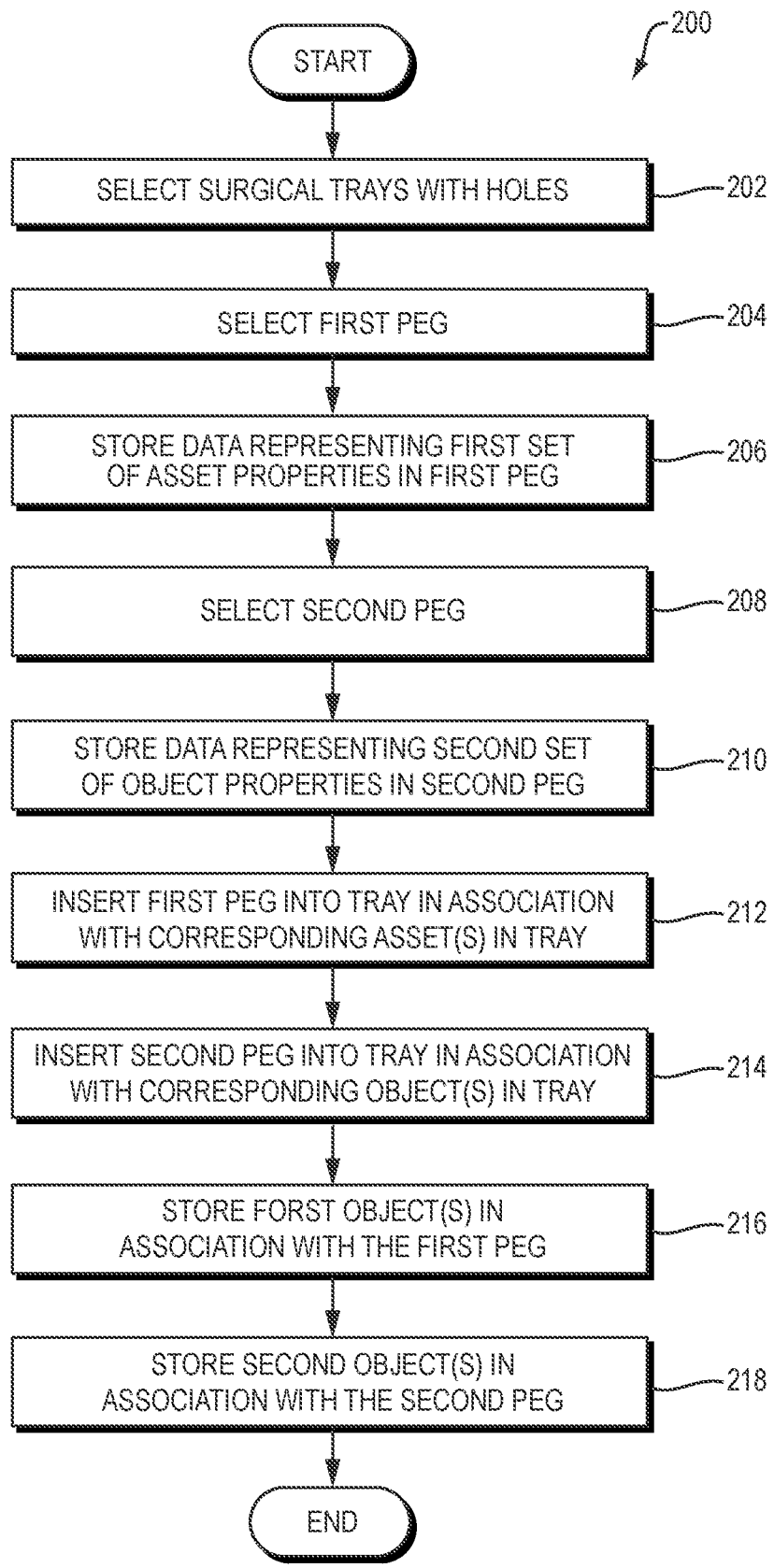
FIG. 2 is a flowchart of a method performed by one embodiment of the present invention to track the removal of objects from a surgical tray.

One embodiment of the present invention is directed to a method for configuring a surgical plating tray using pegs implemented according to embodiments of the present invention, such as pegs of any of the kinds illustrated in FIGS. 1A-1B. Referring to FIG. 2, a flowchart is shown of such a method 200 according to one embodiment of the present invention. The method 200 includes selecting a tray having a plurality of holes suitable for containing surgical assets and/or pegs implemented according to embodiments of the present invention (FIG. 2, operation 202). A first set of asset properties is identified, such as a set of properties of a first kind of asset (e.g., screw). The terms "asset," "supply," and "object" are used interchangeably herein. Examples of assets, as that term is used herein, are surgical assets, such as implants, tools, instruments, and one-time use non-implantable objects, such as k-wires, drill bits, and templates. The first set of properties may include, for example, any one or more of the following, in any combination: manufacturer, model number, part number (e.g., manufacturer's part number and/or federal device identifier (DI)), stock keeping unit (SKU), length, and width. A first peg implemented according to an embodiment of the present invention, such as any of the pegs disclosed herein, is selected (FIG. 2, operation 204), and data representing some or all of the first set of asset properties is stored in a first machine-readable object in the first peg (FIG. 2, operation 206).

A second set of asset properties is identified, such as a set of properties of a second kind of asset (e.g., screw). The second set of properties may include any one or more of the kinds of properties described above. The second set of properties may differ from the first set of properties in whole or in part. For example, the second set of properties may include a SKU or part number that differs from the SKU or part number of the first set of properties. A second peg implemented according to an embodiment of the present invention, such as any of the pegs disclosed herein, is selected (FIG. 2, operation 208), and data representing some or all of the second set of object properties is stored in a second machine-readable object in the second peg (FIG. 2, operation 210).

Note that operations 208 and 210 effectively repeat operations 204 and 206, but for a second peg and second machine-readable object. Operations 204 and 206 may be repeated for any additional number of pegs and corresponding machine-readable objects.

The first peg is inserted into the tray in a first hole in association with one or more corresponding assets (FIG. 2, operation 212). The assets that correspond to the first peg have the properties that are stored in the machine-readable object in the first peg. For example, if the data in the machine-readable object in the first peg indicates a particular screw length, then the assets that correspond to the first peg are screws which have the particular screw length.

The association between the first peg and the corresponding asset(s) may take any of a variety of forms. For example, if the first peg has a directional member, then the directional member of the first peg may be oriented (e.g., rotated) so that it points towards the asset(s) corresponding to the first peg. As another example, if the first peg is stored in a particular slot (e.g., the topmost or bottommost slot) in a row of slots in the asset tray, then the asset(s) that correspond to the first peg may be stored in other slots in the same row as the first peg in the asset tray. These are both examples of associations between the first peg and its corresponding assets.

Similarly, the second peg is inserted into the tray in a second hole in association with one or more corresponding assets (FIG. 2, operation 214). The assets that correspond to the second peg have the properties that are stored in the machine-readable object in the second peg. For example, if the data in the machine-readable object in the second peg indicates a particular screw length, then the assets that correspond to the second peg are screws which have the particular screw length. The association between the second peg and the corresponding asset(s) may take any of a variety of forms, such as any of the forms described above in connection with the first peg and its corresponding asset(s).

Operation 214 may be repeated for any additional number of pegs. Furthermore, any of the pegs may be inserted into more than one hole in the tray.

One or more assets (e.g., screws) of the type represented by the data in the machine-readable object of the first peg are inserted into the surgical tray (FIG. 2, operation 216). One or more assets (e.g., screws) of the type represented by the data in the machine-readable object of the second peg are inserted into the surgical tray (FIG. 2, operation 416). Note that operation 418 effectively repeats operation 416, but for a second peg and corresponding type of asset. Operation 418 may be repeated for any additional number of pegs and corresponding assets.

The result of performing method 200 is to populate an asset tray, with pegs and corresponding assets (e.g., screws), in a manner that associates each of the pegs with its corresponding asset(s). The association between each peg and its corresponding asset(s) may, for example, be visually identifiable, such as by a human or machine. As will be described in more detail below, this enables the removal of such assets from the tray to be detected and tracked.

The order of the steps shown in FIG. 2 is merely an example and does not constitute a limitation of the present invention. The steps of method 200 may be performed in orders other than the order shown in FIG. 2. For example, steps 216 and 218 may be performed before steps 212 and 214. As another example, steps 206, 206, 208, and 210 may be performed after steps 216 and 218.

Embodiments of the present invention include methods for reading data from machine-readable objects (such as the machine-readable objects in cap pieces 102a-b in FIGS. 1A-1B) to track the removal of objects (e.g., surgical assets) from a surgical tray. For example, referring to FIG. 3, a flowchart is shown of a method 300 for tracking the removal of objects from a tray 402 according to one embodiment of the present invention. Referring to FIG. 4, a diagram is shown of a system 400 for performing the method 300 of FIG. 3 according to one embodiment of the present invention.

Figure 3:
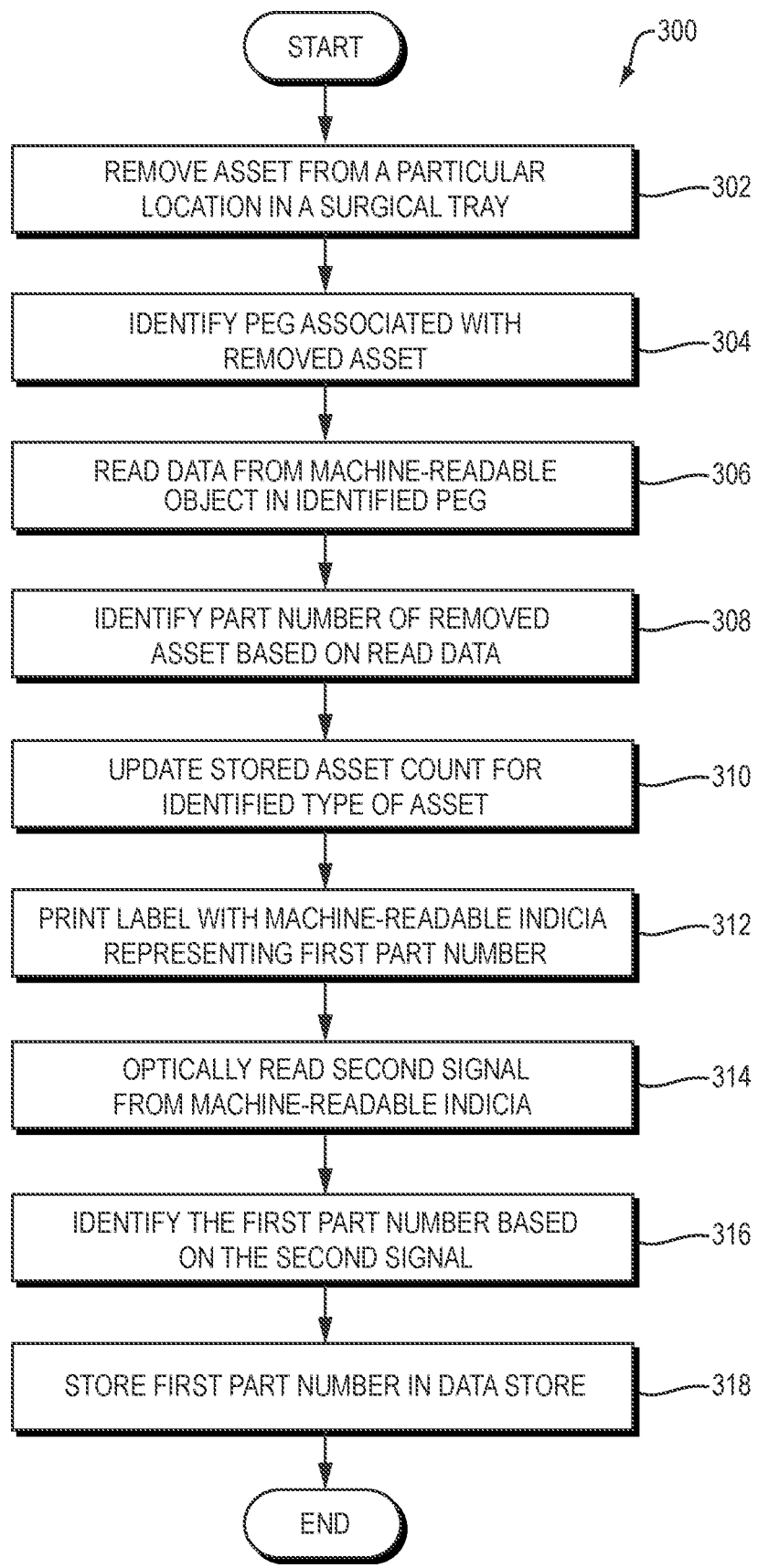
FIG. 3 is a flowchart of a method for tracking the removal of objects from a tray according to one embodiment of the present invention.
Figure 4:
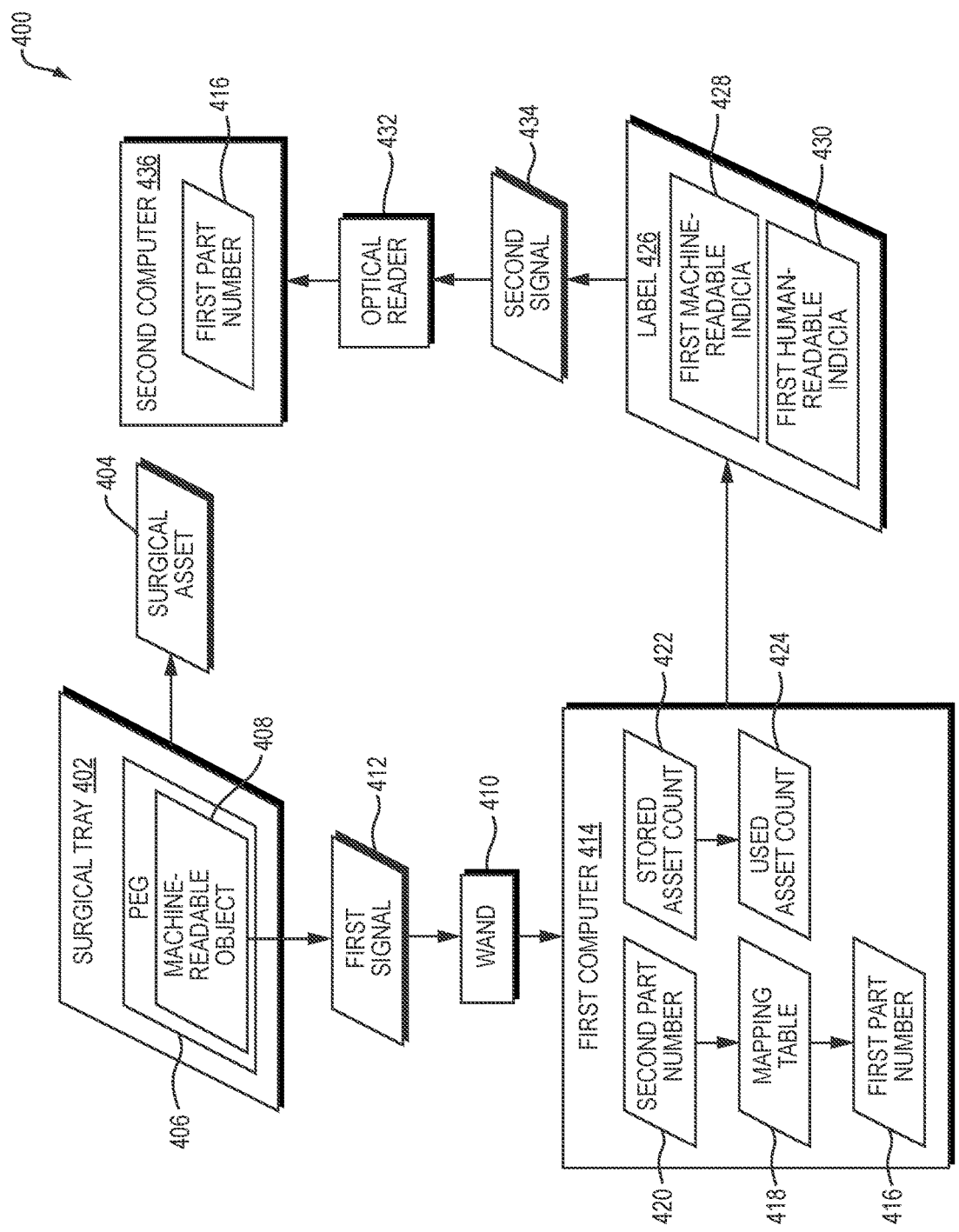
FIG. 4 is a diagram of a system for performing the method of FIG. 3.

A first surgical asset 404 (e.g., screw) is removed from a particular location (e.g., hole) of the tray 402 (FIG. 3, operation 302). A peg 406 that is associated with the first asset 404 and/or with the particular location of the tray 402 is identified (FIG. 3, operation 304). The peg 406 may be identified in any of a variety of ways. For example, a human operator may identify the peg 406 that is associated with the first asset 404 by visual inspection of the tray and the pegs and assets that it contains. For example, if the identified peg 406 has a directional member, then if the peg 406's directional member points to the removed surgical asset 404 (e.g., while the surgical asset 404 is still in the tray, i.e., before operation 302), then the peg 406 may be identified as the peg that is associated with the surgical asset 404. As another example, if the surgical asset 404 is in a row of slots, and the peg 406 is in another slot in that row, then the peg 406 may be identified as the peg that is associated with the surgical asset 404.

As described above, a peg in the tray 402 may be associated with more than one surgical asset. As this implies, if the method 300 is repeated in connection with the removal of multiple assets from the tray 402, then the same peg may be identified as pointing to those multiple assets.

One or more units of data are read from a first machine-readable object 408 contained within the identified peg 406 (FIG. 3, operation 306). Such data may be read in any of a variety of ways. For example, a wand 410 may be positioned (e.g., by a human operator) over the surface of the first machine-readable object 408, thereby causing the wand to read some or all of the data from the first machine-readable object 408. The wand 410 or other reading device may be triggered to read data from the first machine-readable object 408 in response to input from the human operator, such as the pressing of a button. In general, reading the data from the first machine-readable object 408 contained within the identified peg 406 may include receiving a first signal 412 (e.g., wirelessly) from the first machine-readable object 408.

The system 400 also includes a first computer 414. The first computer 414 may receive the first signal 412, or another signal containing the same information as the first signal 412. The computer may automatically identify, based on the first signal 412, a first part number 416 of the first surgical asset 404 (FIG. 3, operation 308). The first part number 416 may be any of a variety of types of part numbers, such as a federal device identifier (DI) of the first surgical asset 404, a manufacturer's part number of the first surgical asset 404, or a part number of the first surgical asset 404 other than the federal DI or the manufacturer's part number. Any such part number may be stored within data in the first machine-readable object 408, in which case the first signal 412 may include information representing that part number, and the identification performed in operation 308 may involve directly identifying the part number within the first signal 412.

Alternatively, for example, the first signal 412 may include information representing a second part number that is different from the first part number 416. For example, the first machine-readable object 408 may include data representing a second part number 420 that is neither a federal device identifier (DI) of the first surgical asset 404 nor a manufacturer's part number of the first surgical asset 404, such as a part number used internally by software that performs the method 300 (referred to herein as an "internal part number"). In this case, the first signal 412 may include data representing the internal part number, and operation 308 may involve identifying the first part number 416 of the first surgical asset 404 (e.g., the federal device identifier (DI) of the first surgical asset 404 or the manufacturer's part number of the first surgical asset 404) based on the internal part number of the first surgical asset 404. For example, a mapping table 418 which stores mappings between internal part numbers and federal device identifiers (DI) and/or manufacturer's part numbers may be stored in a non-transitory computer-readable medium (e.g., within or coupled to the first computer 414). Operation 308 may involve using the mapping table 418 to map the internal part number of the first surgical asset 404 to the federal device identifier (DI) of the first surgical asset 404 or the manufacturer's part number of the first surgical asset 404, thereby identifying the federal device identifier (DI) of the first surgical asset 404 or the manufacturer's part number of the first surgical asset 404 based on the internal part number of the first surgical asset 404.

Operation 308 may perform any of a variety of other mappings of part numbers, either instead of or in addition to the mapping described above. For example, the first signal 412 may include information representing an internal part number of the first asset 404, in which case operation 308 may involve either: (1) mapping the internal part number of the first asset 404 to the federal DI of the first asset 404, and then mapping the federal DI of the first asset 404 to the manufacturer's part number of the first asset 404; or (2) mapping the internal part number of the first asset 404 to the manufacturer's part number of the first asset 404, and then mapping the manufacturer's part number of the first asset 404 to the federal DI of the first asset 404.

More generally, the first signal 412 may include information representing any one or more of the following, for example: (1) the internal part number of the first asset 404; (2) the federal DI of the first asset 404; and (3) the manufacturer's part number of the first asset 404. Operation 308 may involve identifying the part number of the first asset 404 as the part number contained within the information in the first signal 412. Alternatively, operation 308 may involve mapping (e.g., using the mapping table 418) the part number contained within the information in the first signal (referred to herein generically as a second part number 420) to any one of (1), (2), and (3) described earlier in this paragraph, and then (optionally) mapping the resulting (mapped) part number to any one of (1), (2), and (3). As shown in FIG. 4, if the machine-readable object 408 includes data representing the second part number 420, then the first signal 412 may include data representing the second part number 420, in which case operation 308 may involve mapping (e.g., using the mapping table 418) to map the second part number 420 to the first part number 416.

Although not shown in FIG. 3, the method 300 may identify additional information about the first asset 404 based on the information in the first signal 412 and/or any additional information identified in operation 308. Examples of information which the method 300 may identify in this way are any one or more of the following, in any combination: a type (e.g., length) of the first asset 404, a manufacturer of the first asset 404, and a price of the first asset 404. The method 300 may identify this additional information in any of a variety of ways, such as by using the information received and/or derived in operation 308 as a key or index into a database or other data store to obtain the additional information.

If the method 300 identifies a type of the first asset 404, then the method 300 may decrement a stored count 422 of the identified asset type (FIG. 3, operation 310). For example, a computer may include a database or other data store containing counts of various types of assets. As a particular example, such a data structure may begin with a count, for each of the asset types initially stored in the tray 402, of the number of assets of that type initially stored in the tray 402. Such a data store may include, for each of one or more assets, additional data about that asset, such as its part number and a unique identifier of the object, such as a unique identifier that is stored in the asset's machine-readable object.

In addition to or instead of decrementing the stored count 422 of the identified asset type, the method 300 may increment a count 424 of the number of assets of the identified asset type that have been removed from the tray 402. For example, the first computer 414 may initially contain data 424 indicating that zero objects of each asset type have been removed from the tray 402, such as when the method 200 of FIG. 2 is performed to initially load the tray 402. Then, as each asset is removed from the tray 402, the method 300 may increment the count 424 of the number of assets of that type that have been removed from the tray 402.

Operations 302-310 may be repeated for any number of assets removed from the tray 402, thereby maintaining an accurate count 424 of the number of assets removed from the tray 402.

The method 300 may print (e.g., on paper or other human-readable medium) a label 426 to include a first machine-readable visual indicia 428 representing the first part number 416 (FIG. 3, operation 312). The first machine-readable visual indicia 428 may, for example, be a bar code or QR code. The method 300 may use a printer of any kind (not shown) to print the label 426. The printer may, for example, be contained with, coupled to, or otherwise in communication with the first computer 414. The method 300 may print additional information on the label 426, such as first human-readable indicia 430 (e.g., characters) representing the first part number 416 and/or additional information about the first asset 404, such as a manufacturer, type, price, and/or name of the first asset 404.

The method 300 may use an optical reader 432 to optically read a second signal 434 from the first machine-readable visual indicia 428 (FIG. 3, operation 314). For example, if the first machine-readable indicia 428 is a bar code, then the optical reader 432 may be a bar code reader, which the method 300 may use to read the bar code. As another example, if the first machine-readable indicia 428 is a QR code, then the optical reader 432 may be a QR code reader, which the method 300 may use to read the QR code. The optical reader 432 may be within, coupled to, or otherwise in communication with a computer, such as the first computer 414, or a second computer 436 within the system 400.

The method 300 may identify the first part number 416 of the first surgical asset 404 based on the second signal 434 (FIG. 3, operation 316). For example, if the first machine-readable indicia 428 is a bar code, then the second signal 434 may include information in the bar code, and the method 300 may identify the first part number 416 based on the information in the bar code. For example, the bar code may represent the first part number 416, in which case the method 300 may identify the first part number 416 directly based on the information in the bar code. As another example, the bar code may represent a third part number (which may, for example, be the same as the second part number 420), in which case the method 300 may identify the first part number 416 based on the third part number, such as by mapping the third part number to the first part number 416. The printing in operation 312 may include, in addition to printing the first machine-readable indicia 428 representing the first part number 416, printing second machine-readable indicia (not shown) representing the third part number on the same label 426 as the first machine-readable indicia 428 representing the first part number 416.

Operations 314 and/or 316 may be performed by, in cooperation with, or under the control of a second computer 436. The first computer 414 and the second computer 436 may be physically distinct from each other. For example, they may be in distinct housings and have distinct processors and memories. As another example, they may execute distinct operating system instances (which may be the same or different types of operating systems). The first computer 414 and the second computer 436 may or may not be coupled to each other or otherwise in communication with each other. For example, the first computer 414 and the second computer 436 may not be coupled to each other by any cabling or wireless connections. As yet another example, the first computer 414 and the second computer 436 may not be coupled to each other over a Local Area Network (LAN). The optical reader 432 may be contained within, coupled to, or otherwise in communication with the second computer 436. The second computer 436 may control the optical reader 432 to optically read the first machine-readable visual indicia 428 in operation 314. The optical reader 432 may provide the second signal 434, or another signal containing the same information as the second signal 434, to the second computer 436. As another example, the second computer 436 may identify the first part number 416 based on the second signal 434 in operation 316. As a result, the second computer 436 may contain a copy of the first part number 416, as shown in FIG. 4.

The method 300 may, based on the first part number 416 identified in operation 316, store, or cause to be stored, the first part number 416 in a non-transitory computer-readable medium, such as a database or other data store (FIG. 3, operation 318). The database may, for example, be or include an electronic health record (EHR) database. Note that a first instance of the first part number 416 may be stored in a first non-transitory computer-readable medium in the first computer 414 (or coupled to or otherwise in communication with the first computer 414), and that a second instance of the first part number 416 may be stored in a second non-transitory computer-readable medium in the second computer 436 (or coupled to or otherwise in communication with the second computer 436). The first and second non-transitory computer-readable media may be physically distinct from each other. For example, they may be a first physical memory in the first computer 414 and a second physical memory in the second computer 436.

As another example, a first instance of the first part number 416 may be stored in a first data store (e.g., a first data structure or database) in the first computer 414 (or otherwise coupled to or in communication with the first computer 414), and a second instance of the first part number may be stored in a second data store (e.g., a second data structure or database) in the second computer 436 (or otherwise coupled to or in communication with the second computer 436). The first and second data stores may not be in communication with each other. As another example, the first and second data stores may not be compatible with each other. For example, the first instance of the first part number may be stored in the first data store in a data format that is not compatible with a second data format in which the second instance of the first part number is stored in the second data store.

Because the first and second computers 414 and 436 may or may not be connected to each other, e.g., over a network, the method 300 may be used to transfer information (e.g., the first part number 416) from the first computer 414 to the second computer 436 efficiently, accurately, and semi-automatically, even when the first computer 414 and the second computer 436 are not in communication with each other, and even when the first computer 414 and the second computer 436 are incompatible with each other or otherwise unable to communicate with each other.

Operations 312-318 may be repeated for one or more assets in addition to the first asset 404. Part numbers for such additional assets may be printed in machine-readable indicia on the same label 426 as the machine-readable indicia for the first part number 416. As a result, the single label 426 may include machine-readable indicia representing part numbers of a plurality of assets.

One aspect of the present invention is directed to a method performed by at least one computer processor executing computer program instructions stored on at least one non-transitory computer-readable medium. The method includes: (A) receiving a first signal from a first machine-readable object; (B) identifying, based on the first signal, a first part number of a first surgical asset; (C) printing a label to include a first machine-readable visual indicia representing the first part number; (D) optically reading a second signal from the first machine-readable visual indicia; (E) identifying the first part number of the first surgical asset based on the second signal; and (F) based on the identifying in (E), causing the first part number of the first surgical asset to be stored in a non-transitory computer-readable medium.

The first part number may, for example, include a federal device identifier (DI) of the first surgical asset. The first part number may, for example, include a manufacturer's part number of the first surgical asset.

Operation (B) may include: (B)(1) identifying, based on the first signal, a second part number of the first surgical asset; and (B)(2) identifying the first part number based on the second part number. The first part number may include a federal device identifier (DI) of the first surgical asset. The first part number may include a manufacturer's part number of the first surgical asset. The first part number may, for example, include neither a federal device identifier (DI) of the first surgical asset nor a manufacturer's part number of the first surgical asset. The method may further include: (G) before (A), storing, in a computer-readable medium, a mapping between the first part number of the surgical asset and the second part number of the surgical asset; and (B)(1) may include identifying the second part number based on the mapping. Operation (C) may further include printing, on the label, a second machine-readable visual indicia representing the second part number. The first part number may include a federal device identifier (DI) of the first surgical asset. The first part number may include a manufacturer's part number of the first surgical asset.

The first signal may include data representing the first part number of the first surgical asset, and (B) may include identifying the first part number based on the data representing the first part number of the first surgical asset.

Operation (B) may include reading the first part number of the first surgical asset from a first data store; and (F) may include storing the first part number of the second surgical asset in a second data store.

The machine-readable object may be in proximity to the first surgical asset. The machine-readable object may point to the first surgical asset.

Operation (B) may further include identifying, based on the first signal, a price of the first surgical asset.

Operation (C) may further include printing, on the label, human-readable visual indicia representing a price of the first surgical asset. Operation (C) may further include printing, on the label, human-readable visual indicia representing a description of the first surgical asset.

The first machine-readable visual indicia may include a bar code. The first machine-readable visual indicia may include a QR code.

The first signal may include a radio-frequency signal, wherein the machine-readable object comprises an RFID tag, and wherein (A) comprises receiving the radio-frequency signal from the RFID tag.

The method may further include: (G) receiving a third signal from a second machine-readable object; and (H) identifying, based on the third signal, a second part number of a second surgical asset; wherein (I) may include printing the label to include a second machine-readable visual indicia representing the second part number; and wherein the method may further include: (I) optically reading a fourth signal from the second machine-readable visual indicia; (J) identifying the second part number of the second surgical asset based on the fourth signal; and (K) based on the identifying in (J), causing the second part number of the second surgical asset to be stored in the computer-readable medium.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more machines, such as computers, computer processors, and/or other elements of a computer system. Such features are either impossible or impractical to implement mentally and/or manually. For example, embodiments of the present invention read data from a machine-readable object, such as by using a wand to read data from a chip. This function cannot be performed by a human manually or mentally.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic discs such as internal hard discs and removable discs; magneto-optical discs; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disc (not shown) or a removable disc. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

What is claimed is:

1. A method performed by at least one computer processor executing computer program instructions stored on at least one non-transitory computer-readable medium, the method comprising:
    (A) receiving a first signal from a first machine-readable object;
    (B) identifying, based on the first signal, a first part number of a first surgical asset;
    (C) printing a label to include a first machine-readable visual indicia representing the first part number;
    (D) optically reading a second signal from the first machine-readable visual indicia;
    (E) identifying the first part number of the first surgical asset based on the second signal; and
    (F) based on the identifying in (E), causing the first part number of the first surgical asset to be stored in a non-transitory computer-readable medium.

2. The method of claim 1, wherein the first part number comprises a federal device identifier (DI) of the first surgical asset.

3. The method of claim 1, wherein the first part number comprises a manufacturer's part number of the first surgical asset.

4. The method of claim 1, wherein (B) comprises:
    (B)(1) identifying, based on the first signal, a second part number of the first surgical asset; and
    (B)(2) identifying the first part number based on the second part number.

5. The method of claim 4, further comprising:
    (G) before (A), storing, in a computer-readable medium, a mapping between the first part number of the surgical asset and the second part number of the surgical asset; and
    wherein (B)(1) comprises identifying the second part number based on the mapping.

6. The method of claim 1, wherein the first signal includes data representing the first part number of the first surgical asset, and wherein (B) comprises identifying the first part number based on the data representing the first part number of the first surgical asset.

7. The method of claim 1, wherein the first machine-readable visual indicia comprises a bar code.

8. The method of claim 1, wherein the first machine-readable visual indicia comprises a QR code.

9. The method of claim 1, wherein the first signal comprises a radio-frequency signal, wherein the machine-readable object comprises an RFID tag, and wherein (A) comprises receiving the radio-frequency signal from the RFID tag.

10. The method of claim 1, further comprising:
    (G) receiving a third signal from a second machine-readable object;
    (H) identifying, based on the third signal, a second part number of a second surgical asset;
    wherein (I) comprises printing the label to include a second machine-readable visual indicia representing the second part number; and wherein the method further includes:
(I) optically reading a fourth signal from the second machine-readable visual indicia;
(J) identifying the second part number of the second surgical asset based on the fourth signal; and
(K) based on the identifying in (J), causing the second part number of the second surgical asset to be stored in the computer-readable medium.

11. A system comprising at least one non-transitory computer-readable medium having computer program instructions stored thereon, the computer program instructions being executable by at least one processor to perform a method, the method comprising:
(A) receiving a first signal from a first machine-readable object;
(B) identifying, based on the first signal, a first part number of a first surgical asset;
(C) printing a label to include a first machine-readable visual indicia representing the first part number;
(D) optically reading a second signal from the first machine-readable visual indicia;
(E) identifying the first part number of the first surgical asset based on the second signal; and
(F) based on the identifying in (E), causing the first part number of the first surgical asset to be stored in a non-transitory computer-readable medium.

12. The system of claim 11, wherein the first part number comprises a federal device identifier (DI) of the first surgical asset.

13. The system of claim 11, wherein the first part number comprises a manufacturer's part number of the first surgical asset.

14. The system of claim 11, wherein (B) comprises:
(B)(1) identifying, based on the first signal, a second part number of the first surgical asset; and
(B)(2) identifying the first part number based on the second part number.

15. The system of claim 14, wherein the method further comprises:

(G) before (A), storing, in a computer-readable medium, a mapping between the first part number of the surgical asset and the second part number of the surgical asset; and wherein (B)(1) comprises identifying the second part number based on the mapping.

16. The system of claim 11, wherein the first signal includes data representing the first part number of the first surgical asset, and wherein (B) comprises identifying the first part number based on the data representing the first part number of the first surgical asset.

17. The system of claim 11, wherein the first machine-readable visual indicia comprises a bar code.

18. The system of claim 11, wherein the first machine-readable visual indicia comprises a QR code.

19. The system of claim 11, wherein the first signal comprises a radio-frequency signal, wherein the machine-readable object comprises an RFID tag, and wherein (A) comprises receiving the radio-frequency signal from the RFID tag.

20. The system of claim 11, wherein the method further comprises:
(G) receiving a third signal from a second machine-readable object;
(H) identifying, based on the third signal, a second part number of a second surgical asset;
wherein (I) comprises printing the label to include a second machine-readable visual indicia representing the second part number; and
wherein the method further includes:
(I) optically reading a fourth signal from the second machine-readable visual indicia;
(J) identifying the second part number of the second surgical asset based on the fourth signal; and
(K) based on the identifying in (J), causing the second part number of the second surgical asset to be stored in the computer-readable medium.

\* \* \* \* \*